(12) United States Patent
Shani (10) Patent No.: US 8,013,211 B2
(45) Date of Patent: Sep. 6, 2011

(54) COMPOSITIONS AND METHODS COMPRISING STINGING CAPSULES/CELLS FOR DELIVERING A BIOLOGICALLY ACTIVE AGENT INTO A PLANT CELL

(75) Inventor: Ziv Shani, Mazkeret Batia (IL)

(73) Assignee: FuturaGene Israel, Ltd., Rehovot (IL)

( * ) Notice: Subject to any disclaimer, the term of this patent is extended or adjusted under 35 U.S.C. 154(b) by 726 days.

(21) Appl. No.: 11/994,949

(22) PCT Filed: Jul. 5, 2006

(86) PCT No.: PCT/IL2006/000779
§ 371 (c)(1),
(2), (4) Date: Feb. 11, 2008

(87) PCT Pub. No.: WO2007/007316
PCT Pub. Date: Jan. 18, 2007

(65) Prior Publication Data
US 2009/0144855 A1  Jun. 4, 2009

Related U.S. Application Data

(60) Provisional application No. 60/696,799, filed on Jul. 7, 2005.

(51) Int. Cl.
| C12N 15/82 | (2006.01) |
| C12N 15/13 | (2006.01) |
| C12N 5/06 | (2006.01) |
| C12N 5/10 | (2006.01) |
| A01N 63/00 | (2006.01) |
| A01N 65/00 | (2009.01) |
| A61K 48/00 | (2006.01) |

(52) U.S. Cl. ........ 800/278; 800/286; 800/288; 800/290; 800/293; 800/300; 800/302; 435/326; 424/93.21; 424/93.7

(58) Field of Classification Search .................. None
See application file for complete search history.

(56) References Cited

U.S. PATENT DOCUMENTS
6,613,344 B2   9/2003 Lotan

FOREIGN PATENT DOCUMENTS
WO   02/26191 A1   4/2002
WO   03/079967 A2   10/2003

OTHER PUBLICATIONS

D'Halluin et al. The Plant Cell 4(12): 1495-1505 (Dec. 1992).*
Kaeppler et al. Theoretical and Applied Genetics 84(5-6): 560-566 (Aug. 1992).*
De Block, M. et al., "Expression of foreign genes in regenerated plants and in their progeny", EMBO J, 3(8):1681-1689 (1984).
Hidaka, M., "Effects of Ca2+ on the Volume of Nematocysts Isolated from Acontia of the Sea Anemone Calliactis Tricolor", Comp Biochem Physiol, 101A(4):737-741 (1992).
Hidaka, M., "Mechanism of Nematocyst Discharge and Its Cellular Control", Adv. Comp. And Environ. Physiol. 15:45-76 (1993).
Holstein, T. et al., "An Ultrahigh-Speed Analysis of Exocytosis: Nematocyst Discharge", Science, 223(4638):830-833 (1984).
Jefferson, R. A. et al., "GUS fusions: B-glucuronidase as a sensitive and versatile gene fusion marker in higher plants", EMBO J., 6(13):3901-3907 (1987).
Lotan, A. et al., "Delivery of a nematocyst toxin", Nature, 375(6531):456 (1995).
Lotan, A. et al., "Toxin Compartmentation and Delivery in the Cnidaria: The Nematocyst's Tubule as a Multiheaded Poisonous Arrow", J Exp Zool, 275(6):444-451 (1996).
Lubbock, R. et al., "Removal of bound calcium from nematocyst contents causes discharge", Nature, 290(5806):500-501 (Apr. 9, 1981).
Songstad, D. D. et al., "Advances in alternative DNA delivery techniques", Plant cell, Tissue and Organ Culture, 40:1-15 (1995).
Tardent, P., "The cnidarian cnidocyte, a high-tech cellular weaponry", BioEssays, 17(4):351-362 (1995).
Tardent, P. et al., "Morphology and morphodynamics of the stenotele nematocyst of *Hydra attenuata* Pall. (Hydrozoa, Cnidaria)", Cell Tissue Res, 224(2):269-290 (1982).
Tournier, V. et al., An efficient procedure to stably introduce genes into an economically important pulp tree (*Eucalyptus grandis* X *Eucalyptus urophylla*), Transgenic Res. 12(4):403-411 (2003).
Weber, J., "Nematocysts (stinging capsules of Cnidaria) as Donnan-potential-dominated osmotic systems", Eur J Biochem, 184(2);465-476 (1989).
International Search Report for PCT/IL2006/000779 dated Oct. 12, 2006 (2 sheets).
International Preliminary Report on Patentability for PCT/IL2006/000779 dated Jan. 10, 2008 (7 sheets).
Written Opinion of the International Searching Authority for PCT/IL2006/000779 dated Oct. 12, 2006 (6 sheets).

* cited by examiner

*Primary Examiner* — David T Fox
(74) *Attorney, Agent, or Firm* — Fennemore Craig, P.C.; Rodney J. Fuller (57) ABSTRACT

The invention relates to stinging cells or isolated capsules and to their use in compositions and methods for efficient delivery of biologically active agents into a plant cell or plant tissue. The biologically active agent to be delivered by the methods of the present invention is selected from a nucleic acid, a peptide, a polypeptide, a plant hormone, an enzyme, an herbicidal agent, an anti-viral agent, an anti-bacterial agent and an anti-fungal agent. Particularly, the invention is related to compositions and methods for the efficient transformation of polynucleotide construct into a plant cell or tissue, to obtain transgenic plants.

43 Claims, 6 Drawing Sheets

COMPOSITIONS AND METHODS COMPRISING STINGING CAPSULES/CELLS FOR DELIVERING A BIOLOGICALLY ACTIVE AGENT INTO A PLANT CELL

RELATED APPLICATION DATA

This application is the U.S. national stage of PCT/IL2006/000779 filed on Jul. 5, 2006, which is based on and claims the benefit of U.S. Provisional Patent Application No. 60/696,799 filed on Jul. 7, 2005, the content of each of which is expressly incorporated herein in its entirety by this reference.

FIELD OF THE INVENTION

The present invention relates to stinging cells or capsules and to the use thereof in compositions and methods for efficient delivery of an agent biologically active in a plant cell into the plant cell or plant tissue, particularly for the efficient transformation of a plant cell or tissue.

BACKGROUND OF THE INVENTION

Plant Transformation

In recent years, advances in molecular biology have allowed mankind to manipulate the genetic complement of animals and plants. Genetic engineering of plants entails the isolation and manipulation of genetic material (typically in the form of DNA or RNA) and the subsequent introduction of the genetic material into plants. Such techniques mainly include methods for delivering a nucleic acid into a plant cell or plant tissue to produce transformed cells, and methods of regenerating transgenic plants from the stably transformed cells. Such technology has led to the development of plants with increased pest resistance, herbicide resistance, plants that are capable of expressing pharmaceuticals and other chemicals and plants that express beneficial agricultural traits, such as increased yield, fiber quality and improved digestibility. Advantageously, such plants not only contain genes of interest, but also remain fertile.

One of the most common delivery methods utilizes Agrobacterium-mediated transformation; other frequently used methods involve direct DNA transfer methods (summarized in: Songstad et al., 1995. Plant cell, Tissue and Organ Culture, 40:1-15), including microprojectile bombardment, electroporation of protoplasts or germinating pollen silicon carbide fibers, electrophoresis, polyethylene glycol (PEG) mediated DNA uptake and microinjection. Of these methods, the Agrobacterium-mediated and the microprojectile bombardment methods are routinely used for plant transformation today.

Although the above-described methods have all been shown to be efficient for plant transformation, each has its disadvantages. For Agrobacterium the major disadvantages include its clone dependent infection efficiency, and the need to eliminate the bacteria after the DNA transformation. In the case of microprojectile bombardment, bombardment results in foreign DNA and chromosomes breaking as well as multiple copy insertion, which are undesirable phenomena.

The current microinjection methods utilizing rough needles are problematic methods, because the plant cell wall represents a barrier to the needles while the vacuolar membrane is easily ruptured by such needles, resulting in the leakage of the hydrolytic vacuolar contents and cell death. The technique is also very slow and requires an expensive micromanipulator and substantial manpower resources (Songstad et al., 1995, supra). In addition, the above-described methods are all limited to the delivery of nucleic acids.

Stinging Capsules

Cnidaria (hydras, sea anemones, jellyfish and corals) are aquatic animals, which possess a variety of compounds that are stored and delivered via specialized capsules (cnidocysts). These capsules form a part of specialized cells termed stinging cells (cnidocytes, nematocytes, ptychocytes and the like). The stinging capsules act as microscopic syringes and serve as a predatory or defense mechanism. The Cnidaria family, which encompasses 10,000 known species, includes sedentary single or colonial polyps and pelagic jellyfish. In some of these species, cnidocytes account for more than 45% of the cells present (Tardent 1995. BioEssays, 17(4):351-362). There are a few dozen known types of cnidocysts (also termed cnidae) including more than 30 varieties of nematocysts found in most Cnidaria and spirocysts, and ptychocysts found mainly in the Cnidaria class Anthozoa (Mariscal 1974. In: Coelenterate biology: reviews and new perspectives, Academic Press, New York).

The ability of the stinging cells to penetrate and insert therapeutic or cosmetic agents into mammalian cells including human cells is disclosed in International Patent Application Publication No. WO 02/26191 and corresponding U.S. Pat. No. 6,613,344, fully incorporated herein by reference. A cnidocyst is a hardened dense capsule containing a highly folded inverted tubule and filled with liquid. The tubule may feature a specialized structure such as a shaft, barb, spine, and/or stylet. In nature, the cnidocyst discharges and releases its tubule into tissue following physical or chemical triggering.

Discharge is initiated by a rapid osmotic influx of water, which generates an internal hydrostatic (liquid) pressure of about 150 atmospheres, forcing capsule rupture and ejection of the tubule (Holstein and Tardent 1984. Science, 223(4638): 830-3). During ejection, the long coiled and twisted tubule is averted and its length increases by 95 percent. Accelerating at 40,000 g, the tubule untwists to generate a torque force, which rotates the tubule several times around its axis. These mechanical processes generate a powerful driving force, which enables efficient delivery of the compounds, the toxins and enzymes stored within the capsule (Lotan et al. 1995. Nature, 375(6531):456; Lotan et al. 1996. J Exp Zool, 275 (6):444-51; Tardent 1995, supra). This process, which occurs within microseconds, is among the most rapid exocytosis events in biology (Holstein and Tardent 1984, supra).

International Patent Application WO03/079967 discloses methods, compositions and devices utilizing stinging cells containing an exogenous polynucleotide encoding a therapeutic or diagnostic agent or a cosmetic agent for delivering the agent into human cells or tissue. The use of stinging cells has hitherto been demonstrated only for the delivery of therapeutic or cosmetic agents to mammals. Plant cells are different from mammalian cells in that they comprise a rigid cell wall apposed to, and external to the plant protoplast. The plant protoplast comprises a plasma membrane enclosing the cell cytoplasm. The presence of a cell wall gives the plants its rigidity and protects the plant protoplast against outside injuries. However, as described above, the cell wall also limits the number of methods that can be utilized efficiently for the delivery of external biologically active agents into the plant protoplasts.

Thus, there is a recognized need for, and it would be highly advantageous to have efficient, easy to use compositions and methods for the delivery of various biologically active agents into the plant cell or plant tissue.

SUMMARY OF THE INVENTION

The present invention relates to compositions and methods utilizing stinging cells or stinging capsules isolated therefrom for the delivery of an agent biologically active in a plant cell into a plant cell or a plant tissue. Particularly, the compositions and methods of the present invention are utilized for the delivery of at least one of a polynucleotide construct, a peptide, a polypeptide, an enzyme, a hormone, a candidate herbicidal agent, anti viral agent, anti bacterial agent and anti fungal agent. The compositions and methods are particularly suitable for the efficient transformation of a polynucleotide construct into a plant cell or tissue.

As described above, the use of a stinging cell or a stinging capsule for the delivery of a therapeutic or cosmetic agent into mammalian cells is known. Surprisingly, it is now shown that stinging capsules or cells can be utilized to deliver an agent biologically active in a plant cell through the rigid plant cell wall into the interior compartment of the cell.

According to one aspect, the present invention provides a composition comprising at least one stinging capsule and at least one agent biologically active in a plant cell, wherein the stinging capsule is capable of delivering the agent into the plant cell.

According to one embodiment, the agent active in a plant cell is a polynucleotide construct capable of being expressed in a plant cell. According to this embodiment the at least one polynucleotide construct comprises at least one plant specific regulatory element.

As used herein, the term "plant specific regulatory element" refers to a non-coding polynucleotide regulating the expression of the polynucleotide in the plant cell. Regulatory elements include, for example, constitutive, inducible or tissue-specific promoters; enhancer elements; termination elements; and transposable elements. The practice of the present invention is not bound to a specific construct and any construct suitable for expression of a polynucleotide within a plant cell as is known to a person skilled in the art can be used.

The polynucleotide can be a DNA or RNA. According to certain embodiments of the present invention the polynucleotide may be selected from a polynucleotide encoding a polypeptide or a functional portion of a polypeptide; a polynucleotide encoding a regulatory factor, such as a transcription factor; a non-coding polynucleotide such as a regulatory polynucleotide; an antisense polynucleotide that inhibits expression of a specified polypeptide; and any other polynucleotide which is exogenous to the target plant to be delivered into the target plant cell.

According to another embodiment the at least one polynucleotide construct further comprises a selectable marker.

According to yet another embodiment the at least one polynucleotide construct is a DNA construct designed for generating siRNA.

According to one embodiment, the composition further comprises a biologically compatible carrier or a stabilizer including but not limited to DEAE-Dextran, poly ethylene glycol (PEG) and the like.

The agent may be encompassed within the stinging capsule or may be adjacent to the stinging capsule.

According to one embodiment, the agent is disposed in a liquid medium stored within the stinging capsule. According to another embodiment, the agent is disposed in a liquid medium surrounding the stinging capsule.

It should be understood that the term "plant cell" refers to a single cell as well as to a plurality of cells, forming a plant callus, a plant tissue, a complete whole plant and any other form of a plurality of plant cells.

According to still another embodiment the at least one stinging capsule is derived from an organism of a class selected from the group consisting of Anthozoa, Hydrozoa and Scyphozoa. Preferably, the at least one stinging capsule is derived from a stinging cell of an organism of a phylum selected from the group consisting of Cnidaria, Dinoflagellata and Myxozoa. According to one currently preferred embodiment, the at least one stinging cell forms a part of at least a tentacle portion of an organism of the phylum Cnidaria.

According to one embodiment, the composition may be in a medium selected from the group consisting of an aqueous solution, a gel, and a semi-solid formulation.

In nature, the stinging cells are used for capturing food and as a defense mechanism. The stinging capsule therefore typically comprises one or more toxin. According to certain embodiments of the present invention the endogenous toxin naturally stored within the at least one stinging capsule is non-functional or substantially non-toxic to plants.

According to another embodiment, the agent biologically active in a plant cell is capable of modulating at least one biosynthetic pathway in a plant cell. According to this embodiment the at least one agent is selected from but not limited to the group consisting of a peptide, a polypeptide, a protein, a plant hormone, an enzyme, a candidate herbicidal agent, an anti-viral agent, an anti-bacterial agents and an anti-fungal agent. The plant hormone is selected from the group consisting of an auxin, a cytokinin, abscisic acid, ethylene and a gibberellic acid or any combination thereof.

The agent may be encompassed within the stinging capsule or may be adjacent to the stinging capsule.

According to yet further aspect the present invention provides a method for transforming a plant cell or a plant tissue, The method comprising the steps of: (a) applying at least one polynucleotide construct to an outer surface of the plant cell or plant tissue; (b) applying at least one stinging capsule to the outer surface of said plant cell or said plant tissue; and (c) triggering a discharge of the at least one stinging capsule to thereby deliver the at least one polynucleotide construct into said plant tissue or plant cell to form a transformed plant cell or tissue.

According to one embodiment the transformation is transient. According to another embodiment the transformation is stable.

According to one embodiment, the agent active in a plant cell is a polynucleotide construct capable of being expressed in a plant cell. According to this embodiment the at least one polynucleotide construct comprises at least one plant specific regulatory element.

Regulatory elements include, for example, constitutive, inducible or tissue-specific promoters; enhancer elements; termination elements; and transposable elements. The practice of the present invention is not bound to a specific construct and any construct suitable for expression of a polynucleotide within a plant cell as is known to a person skilled in the art can be used.

According to one embodiment, the at least one polynucleotide construct and the at least one stinging capsule are applied as a single combined composition. According to this embodiment, the composition may be in a medium selected from the group consisting of an aqueous solution, organic or organic cosolvent solution, a gel, and a semi-solid formulation.

According to one embodiment, the at least one polynucleotide construct comprises a selection marker. Selection markers are well known in the art, and the selection technique may vary depending upon the selection marker used. According to one embodiment, the selection marker is a gene inducing antibiotic resistance, enabling the survival of the transformed plant cells/tissue in a medium containing the antibiotic as a selection agent. According to another embodiment, the selection marker is a reporter gene. The selection marker may be any reporter gene, which confers to a cell comprising said gene a characteristics that can be used for selection. According to certain embodiments, this reporter gene is selected from the group consisting of a gene encoding a fluorescent protein, a gene encoding chemiluminescent protein, a gene encoding protein having a detectable enzymatic activity and the like, as is known to a person skilled in the art.

According to yet another embodiment the at least one polynucleotide construct is a DNA construct designed for generating siRNA.

According to one embodiment, the composition further comprises a biologically compatible carrier or stabilizer such as DEAE-Dextran, poly ethylene glycol (PEG) and the like.

The agent may be encompassed within the stinging capsule or may be adjacent to the stinging capsule.

According to one embodiment, the agent is disposed in a liquid medium stored within the stinging capsule. According to another embodiment, the agent is disposed in a liquid medium surrounding the stinging capsule. According to yet another embodiment, the at least one stinging capsule is capable of delivering the agent into the plant cell. It should be understood that the term "plant cell" refers to a single cell as well as to a plurality of cells, forming a plant callus, a plant tissue, a complete whole plant and any other form of a plurality of plant cells.

According to still another embodiment the at least one stinging capsule is derived from an organism of a class selected from the group consisting of Anthozoa, Hydrozoa and Scyphozoa. Preferably, the at least one stinging capsule is derived from a stinging cell of an organism of a phylum selected from the group consisting of Cnidaria, Dinoflagellata and Myxozoa. According to one currently preferred embodiment, the at least one stinging cell forms a part of at least a tentacle portion of an organism of the phylum Cnidaria.

In nature, the stinging cells are used for capturing food and as a defense mechanism. The stinging capsule therefore typically comprises toxin(s). According to certain embodiments of the present invention the endogenous toxin naturally stored within the at least one stinging capsule is non-functional or substantially non-toxic to plants.

According to one embodiment, the at least one polynucleotide construct is disposed in a liquid stored within the stinging capsule. According to another embodiment, the at least one polynucleotide construct is disposed in a liquid surrounding the stinging capsule.

According to one embodiment the step of triggering the discharge of the at least one stinging capsule is affected by a change in pH, a chemical substance, a mechanical force, an electrical force or contact between the at least one stinging capsule and the outer surface of the plant cell or plant tissue.

According to another aspect the present invention provides a method of delivering at least one biologically active agent into a plant cell or plant tissue, the method comprising the steps of: (a) applying a composition comprising the at least one biologically active agent to a outer surface of the plant cell or plant tissue; (b) applying at least one stinging capsule to the outer surface of the plant cell or plant tissue; and (c) triggering a discharge of the at least one stinging capsule to thereby deliver said at least one biologically active agent into said plant cell or plant tissue.

According to certain embodiments of the present invention, the biologically active agent is selected from the group consisting of a nucleic acid, a peptide, a polypeptide, a plant hormone, an enzyme, a herbicidal agent, an anti-viral agent, anti bacterial agents and an anti-fungal agent.

According to one embodiment, the biologically active agent is a nucleic acid. The nucleic acid can be an isolated exogenous polynucleotide, homologous or heterologous to the genome of the target plant cell or in the form of a nucleic acid construct as described herein above.

According to other embodiments, the biologically active agent is a peptide, a polypeptide or a protein.

According to certain embodiments, the amino acid, polypeptide or enzyme is injected into the plant cell to study its effect on biological activities within the plant cell. For example, injecting labeled proteins can be used to track their destination in the plant cell; injection of specific combinations of several polypeptides can be performed to elucidate their interaction within the plant cell.

According to another embodiment, the amino acid, polypeptide or enzyme is injected into the plant cell to affect its activity, for example to affect the cell resistance to herbicides, fungi, bacteria, viruses, abiotic stress etc.

The biologically active agent may be encompassed within the stinging capsule or may be adjacent to the stinging capsule.

According to one embodiment, the biologically active agent is disposed in a liquid stored within the stinging capsule. According to another embodiment, the biologically active agent is disposed in a liquid surrounding the stinging capsule. According to yet another embodiment, the at least one stinging capsule is capable of delivering the biologically active agent into the plant cell.

According to one embodiment the step of triggering the discharge of the at least one stinging capsule is affected by a change in pH, a chemical substance, a mechanical force, an electrical force or contact between the at least one stinging capsule and the outer surface of the plant cell or plant tissue.

According to another embodiment the at least one stinging capsule is derived from an organism of a class selected from the group consisting of Anthozoa, Hydrozoa and Scyphozoa. Preferably, the at least one stinging capsule is derived from a stinging cell of an organism of a phylum selected from the group consisting of Cnidaria, Dinoflagellata and Myxozoa. According to one currently preferred embodiment, the at least one stinging cell forms a part of at least a tentacle portion of an organism of the phylum Cnidaria. According to certain embodiments of the present invention the endogenous toxin naturally stored within the at least one stinging capsule is non-functional or substantially non-toxic to plants.

According to a further aspect, the present invention provides a method of producing transgenic plants, the method comprising the steps of: (a) applying a composition comprising at least one polynucleotide construct to an outer surface of a plant cell or plant tissue; (b) applying at least one stinging capsule to the outer surface of the plant cell or the plant tissue; (c) triggering a discharge of the at least one stinging capsule to thereby deliver the at least one polynucleotide construct into said plant cell or plant tissue to form a stably transformed plant cell or tissue; and (c) regenerating a transgenic plant from the stably transformed cell or tissue.

According to one embodiment, the at least one polynucleotide construct and at least one stinging capsule are applied as a single combined composition.

According to yet further aspect, the present invention provides a method of screening for activity of a biologically active agent within a plant tissue, the method comprising the steps of: (a) applying a composition comprising a plurality of stinging capsules comprising the biologically active agent onto a support in a predetermined pattern; (b) contacting the plant tissue with the plurality of stinging capsules; (c) triggering a discharge of said plurality of stinging capsules to thereby deliver said biologically active agent into said plant tissue and (d) detecting the activity of said biologically active agent within the plant cell.

According to one embodiment, the biologically active agent is selected from the group consisting of a polynucleotide, a peptide, a polypeptide, an enzyme, a hormone, an herbicidal agent, an anti viral agent, an anti bacterial agent and an anti fungal agent According to one embodiment, each of the plurality of stinging capsules can comprise the same biologically active agent. Alternatively, the plurality of stinging capsule comprises a plurality of biologically active agents.

According to another embodiment the stinging capsules are attached to a support.

According to further embodiment, the support is selected from the group consisting of a foil, a glass and a plastic.

According to yet another embodiment, the composition comprising the stinging capsules is formulated in a form enabling the application of the stinging capsules onto the support in a pre-determined pattern.

These and further embodiments will be better understood in conjugation with the description, figures and claims below.

BRIEF DESCRIPTION OF THE DRAWINGS

FIG. 1 shows pBI121 construct for transforming a tobacco plant using the compositions and methods of the invention. The TDNA region contains the NPTII (kanamycin resistance) gene under the NOS promoter as a selection marker and the beta-glucoronidase gene under the CaMV 35S Promoter as a visual marker.

FIG. 2 shows a schematic illustration of transferring a DNA fragment into a plant cell by an isolated stinging cell/capsule. Isolated cell/capsule pre-loaded with the DNA fragment is added to plant tissue or cells (A), and, after stinging is triggered a discharge of the DNA fragment occurs (B).

FIG. 3 shows a schematic illustration of transferring a DNA fragment into a plant cell by an isolated stinging cell/capsule. Isolated cell/capsule and DNA fragment are added to plant tissue or cells (A), and after stinging is triggered the DNA fragment enters the plant cell (B). The capsule, which then penetrates to the cytoplasm or directly to the nucleus, injects, propels or pumps the DNA load into the cell FIG. 4 shows a schematic illustration of preparing a DNA construct containing 35SΩ promoter and GUS gene. The DNA fragment containing the GUS gene and the NOS terminator was isolated from the pBI121 construct using BamIII and EcoRI and was inserted into pUC18 plasmid, downstream of the 35SΩ promoter. In order to isolate the 35SΩ-GUS-NOS terminator construct pUC-35SΩ-GUS-NOS terminator was digested with HindIII and EcoRI, the DNA was extracted by chloroform and ethanol precipitation and was resuspended by water. A mixture of the two DNA fragments was used for the plant transformation using the compositions and methods of the present invention.

FIG. 5 shows Gus expression in transformed cells using the compositions and methods of the present invention in tobacco explants. Transformed areas can be seen as small dark spots on the leaf surface.

FIG. 6 shows stinging capsules after releasing the DNA fragment into the plant tissue in the transformed leaves as observed under light microscope (the penetration point are marked by a half-circle symbol).

DETAILED DESCRIPTION OF THE INVENTION

The present invention provides compositions and methods utilizing stinging cells or capsules for the delivery of a biologically active agent into a plant cell, an isolated plant tissue, an intact plant organ or a whole plant. Particularly, the present invention relates to the use of the composition to efficiently transform a plant cell or tissue with a polynucleotide construct. Specifically, the present invention relates to the use of stinging cells (cnidocytes) or to stinging capsules isolated therefrom (cnidocysts).

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Furthermore, it is to be understood that the phraseology and terminology employed herein is for the purpose of description and should not be regarded as limiting.

Throughout history, man has exploited or imitated naturally occurring processes, e.g., biological processes, for the advancement of scientific fields such as medicine, agriculture and plant biotechnology. As is further described herein, the present invention exploits the unique delivery mechanism of stinging cells, such as cnidocytes or isolated stinging capsules such as cnidocysts, for the delivery of biologically active agents into the cells or tissue of a plant, including dicotyledonous plant and monocotyledonous plants.

By utilizing isolated stinging cells or capsules for delivery of a biologically active agent of choice, the present invention enables easy, efficient, non-destructive and species independent delivery of the biologically active agent into a single plant cell or a plurality of cells including plant tissue, tissue explants, isolated plant organ and intact complete plants. Specifically, the present invention provides compositions and method for efficient transformation of a polynucleotide construct into a plant cell, wherein the transformation may be transient or stable. Superior over hitherto known methods of delivery and transformation, the use of the stinging cells or capsules for delivery and transformation enables an accurate and localized delivery of the biologically active agent. Unexpectedly, the delivery system of stinging capsule is capable of inserting a biologically active agent through the rigid plant cell wall and the cell plasma membrane into the plant protoplast. The present invention enables precise control over the depth of penetration and as such the tissue region of delivery. The tubules within the capsule are capable of penetrating through a tissue to a depth of up to 800 microns, depending on the tissue origin and the type of the stinging cell from which the tubules are discharged. As such, different stinging cell/capsule types can be utilized for delivery into different tissue regions or depths. Typically, a plant cell width of approximately 20 microns can easily be traversed by the tubule. In one embodiment of the invention, the tubule can penetrate through one or several cell layers depending on the tissue and plant species.

As used herein, the phrase "stinging cell" refers to specialized cells (e.g. cnidocytes or nematocytes) present in, for example, all members of the phylum Cnidaria, Myxozoa, and Dinoflagellata. A stinging cell contains the "stinging capsule" which houses the delivery tubule.

As used herein, the term "transformation" refers to the introduction of a polynucleotide construct (i.e. a nucleic acid construct or a polynucleotide described herein above) into a plant cell, either in culture or into the tissues of a plant. The polynucleotide construct may integrate into the host cell genome ("stable transformation") or be expressed without such integration ("transient transformation").

The term "transient transformation" or "transiently transformed" refers to the introduction of one or more polynucleotide constructs into a cell in the absence of integration of the exogenous polynucleotide into the host cell's genome. Transient transformation may be detected by, for example, enzyme-linked immunosorbent assay (ELISA), which detects the presence of a polypeptide encoded by one or more of the exogenous polynucleotides. Alternatively, transient transformation may be detected by detecting the activity of the protein (e.g. β-glucuronidase) encoded by the exogenous polynucleotide. The term "transient transformant" refers to a cell which has transiently incorporated one or more exogenous polynucleotides. In contrast, the term "stable transformation" or "stably transformed" refers to the introduction and integration of one or more exogenous polynucleotides into the genome of a cell. Stable transformation of a cell may be detected by Southern blot hybridization of genomic DNA of the cell with nucleic acid sequences which are capable of binding to one or more of the exogenous polynucleotides. Alternatively, stable transformation of a cell may also be detected by enzyme activity of an integrated gene in growing tissue or by the polymerase chain reaction of genomic DNA of the cell to amplify exogenous polynucleotide sequences. The term "stable transformant" refers to a cell which has stably integrated one or more exogenous polynucleotides into the genomic or organellar DNA. It is to be understood that a plant or a plant cell transformed with the polynucleotide constructs and/or vectors of the present invention can be transiently as well as stably transformed.

The term "construct" as used herein refers to an artificially assembled or isolated polynucleotide which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto. The different elements may also be included in separate DNA fragments rather than on a single DNA fragment.

By "operatively linked", as used herein, is meant that said regulatory elements, including for example, a promoter and an enhancer, are capable of causing expression of said polynucleotide or nucleic acid fragment in a plant cell. Preferably, said regulatory element is upstream of said polynucleotide or nucleic acid fragment and said terminator is downstream of said polynucleotide or nucleic acid fragment.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "transgenic" when used in reference to a plant or seed (i.e., a "transgenic plant" or a "transgenic seed") refers to a plant or seed that contains at least one heterologous gene in one or more of its cells. The term "transgenic plant material" refers broadly to a plant, a plant structure, a plant tissue, a plant seed or a plant cell that contains at least one heterologous gene in at least one of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "homology", as used herein, refers to a degree of sequence similarity in terms of shared amino acid or nucleotide sequences. There may be partial homology or complete homology (i.e., identity). For amino acid sequence homology amino acid similarity matrices may be used as are known in different bioinformatics programs (e.g. BLAST, FASTA, Smith Waterman). Different results may be obtained when performing a particular search with a different matrix. Degrees of homology for nucleotide sequences are based upon identity matches with penalties made for gaps or insertions required to optimize the alignment, as is well known in the art (e.g. Altschul S. F. et al., 1990, J Mol Biol 215(3):403-10; Altschul S. F. et al., 1997, Nucleic Acids Res. 25:3389-3402).

As used herein, the term "nucleic acid" refers to a nucleic acid construct or to a polynucleotide construct. According to the present invention, a polynucleotide construct comprises at least one exogenous polynucleotide and one or more regulatory elements to confer functional expression of the exogenous polynucleotide in the transformed plant cell.

As used herein, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The terms "polypeptide," "peptide" and "protein" are used interchangeably herein to refer to a polymer of amino acid residues. The terms apply to amino acid chains of any length, in which one or more amino acid residues, whether artificial chemical analogue of a corresponding naturally occurring amino acid or naturally occurring amino acid, are linked by covalent peptide bond.

The Cnidaria phylum represents about 10,000 species including sedentary single or colonial polyps and pelagic jellyfish. There are at least three-dozen types of cnidae described in the literature including more than 30 varieties of nematocysts found in most Cnidaria and spirocysts and ptychocysts found mainly in the Cnidaria class Anthozoa (Mariscal 1974, supra).

Although cnidae are characteristic of Cnidaria they can be found in two other groups: the Myxozoa and the Dinoflagellata. Until recently Myxozoan were classified as a protozoa parasite; however, based on phylogenetic analyses of 18S ribosomal RNA sequences it was suggested that the Myxozoa should be grouped in the metazoan phylum (Smothers et al. 1994. Science, 265(5179):1719-21). Anderson et al. (1998. Science, 265(5179):1719-21) placed the Myxozoa with the Bilateria, whereas Siddall et al. suggested that the Myxozoa belongs as a group to the Cnidaria phylum (Siddall et al. 1995. J Parasitol, 81(6):961-7). Myxozoan cnidae are very similar in their morphogenesis and mature structure to the Cnidarian cnidae. Formation of cnidae can be found in the protozoa Dinoflagellata, specifically in the colonial Dinoflagellate Polykrikos. D. polykrikos produces two distinct organelles: the nematocyst and the taeniocyst that are organized as a complex. The Polykrikos nematocyst (cnida) has a similar mature structure of Cnidarian cnida.

Thus, according to one aspect, the present invention provides a composition comprising at least one agent active in a plant cell, and at and at least one stinging capsule.

The unique delivery composition of the present invention enables transfer of agents that are specifically active in a plant cell.

Thus, according to one embodiment, the agent active in a plant cell is a polynucleotide construct comprising at least one isolated polynucleotide and at least one plant-specific regulatory element conferring expression of the polynucleotide in the plant cell.

According to another embodiment, the agent active in a plant cell is a plant hormone. According to one embodiment, the plant hormone is selected from the group consisting of an auxin, a cytokinin, abscisic acid, ethylene and gibberellic acid.

According to another embodiment, the agent active in a plant cell is an herbicide.

According to yet another embodiment, the agent active in a plant cell is an agent for combating a plant disease selected from the group consisting of anti-fungal agents, anti bacterial agents and anti-viral agents.

The stinging capsule according to the teachings of the present invention can be an isolated stinging capsule or alternatively it can form a part of a stinging cell. According to certain embodiments of the present invention, the stinging capsule or cell is derived from an organism of the phylum Cnidaria, Myxozoa, or Dinoflagellata.

The stinging cell or capsule utilized by the present invention is preferably derived from an organism of the class Anthozoa, Hydrozoa or Scyphozoa. More specifically, the stinging cell/capsule utilized by the present invention can be derived from, for example, subclasses Hexacorallia or Octocorallia of the class Anthozoa, (mostly sea anemone and corals), subclasses Siponophora or Hydroida of the class Hydrozoa, or from subclasses Rhisostomeae or Semastomeae of the class Scyphozoa.

In addition, stinging cells from other sources can also be utilized by the present invention. Inactivation of endogenous toxins found within the stinging cell can be affected prior to use via one of several methods, including but not limited to, temperature or chemical denaturation, enzymatic inactivation and ligand inactivation (e.g., Fab fragment of an antibody).

As described in U.S. Pat. No. 6,613,344, incorporated herein in its entirety by reference, incubating isolated cnidocysts at 45° C. for several hours or, alternatively, at a high temperature of 70-95° C. for several minutes can efficiently and easily inactivate toxins endogenous to cnidocysts. Incubation of cnidocysts at 45° C. for 22 hours does not damage or trigger activation of the cnidocyst. Such conditions are effective in denaturing polypeptides stored within the cnidocyst, such as the polypeptide toxins and enzymes delivered by the tubule of the cnidocyst. It will be appreciated that since organisms of, for example, the phylum Cnidaria inhabit aquatic environments, which are characterized by temperatures well below 30° C., polypeptides stored within their stinging capsules can be denatured via incubation in temperatures well above 30° C.

The stinging cell or the stinging capsule of the present invention can be isolated from a cell extract prepared from organs or parts of an organism, which contain the stinging cells (for example a whole hydra or tentacle). Alternatively, stem cells, which give rise to cnidocytes or cnidocysts, can be isolated and cultured. It will be appreciated that the composition of the present invention can also directly utilize the organs, tentacles, or parts of an organism, and the whole organism (hydra for example), which contain the stinging cells without the need for isolating individual stinging cells or for isolating the capsules from the cells.

According to another aspect, the present invention provides a method of delivering at least one biologically active agent into a plant cell or plant tissue, the method comprising the steps of: (a) applying a composition comprising the at least one biologically active agent and at least one stinging capsule to an outer surface of the plant tissue or plant cell; and (b) triggering a discharge of the at least one stinging capsule to thereby deliver said at least one biologically active agent into said plant tissue or plant cell.

According to an additional aspect the present invention provides a method of delivering at least one biologically active agent into a plant cell or plant tissue, the method comprising the steps of: (a) applying a composition comprising the at least one biologically active agent to an outer surface of the plant cell or plant tissue; (b) applying at least one stinging capsule to the outer surface of the plant cell or plant tissue; and (c) triggering a discharge of the at least one stinging capsule to thereby deliver said at least one biologically active agent into said plant cell or plant tissue.

According to one embodiment of the present invention, the biologically active agent is disposed within the liquid stored in the stinging cell or the stinging capsule (FIG. 2). In such a case, the stinging cell or the isolated capsule is loaded with the agent via any one of several methods generally known in the art including, but not limited to, diffusion, electroporation, liposome fusion, microinjection and the like.

Alternatively and according to another embodiment of the present invention, the agent is disposed in a liquid surrounding the stinging cell or the isolated capsule (FIG. 3). In such a case, the stinging capsule's natural mechanism of osmotically collecting liquid from the environment following triggering (further detailed in the background section hereinabove) pumps the biologically active agent into the stinging cell just prior to or during the discharge.

In yet another embodiment, the agent is disposed in a liquid medium surrounding the stinging cell or the isolated capsule. In such a case, the act of discharge following triggering may be sufficient to propel, pump or draw the biologically active agent into the target cell or tissue.

The two alternatives of methods of loading the biologically active agent described above may be equally used, since the stinging capsule is highly permeable to water and molecules.

It has been previously shown that alkali ions, monovalent ions, divalent ions, or small organic cations such as $Tris^+$ or $choline^+$, penetrate cnidocysts and accumulate inside without affecting the properties of the stinging cell or capsule. Studies performed by Lubbock & Amos in order to understand the effect of calcium on capsule discharge (1981. Nature, 290 (5806):500-501) have shown that in the predischarged state the cnida wall is permeable to water and to charged molecules of relatively low molecular weight like bromophenol blue (MW 670) and fluoresceinate (MW 376). Hidaka, who investigated the mechanism of capsule discharge (1992, Comp Biochem Physiol, 101A(4), 737-741; 1993, Adv. Comp. and Environ. Physiol. 15, 45-76) demonstrated that cnidocysts stained with toluidine blue (MW 306) released the blue stain through the tubule when discharged, leaving the capsule completely clear. These studies demonstrate that any low molecular weight biologically active agents can be loaded into stinging cells through simple diffusion; can be stored in the stinging capsule; and can be injected into the target tissue upon capsule discharge.

Loading an agent active in a plant cell according to the teaching of the present invention prior to or during discharge can be therefore easily achieved.

As mentioned hereinabove, during the discharge process, the immediate liquid surrounding the stinging cell is pumped into the capsule and than injected via the tubule. Since the surrounding liquid is pumped into the cnida under extremely high pressures over a short period of time it is highly plausible that high molecular weight molecules, such as polynucleotides can penetrate the capsule and be delivered via the tubule upon discharge. Moreover, the powerful and fast penetration of the tubule into the plant cell may propel or draw the surrounding liquid, including the adjacent molecules into the cell without actually injecting them within the capsules.

Delivery of a biologically active agent according to the present invention can be affected by applying the composition comprising the agent and at least one stinging capsule to the outer surface of a plant cell or to the outer layers of a plant tissue. Following application, the stinging cells or the isolated capsules are triggered (as is further described herein below) and the biologically active agent is thereby delivered by the tubule into the cell.

Alternatively, the biologically active agent can be applied onto the tissue or in the medium or solution surrounding the tissue, followed by application of stinging cell(s) or stinging capsules to the same region. Upon triggering, the biologically active agent is pumped into the stinging cells or into the capsules (as is further described herein below) and is thereby delivered via the tubule into the cell or tissue or propelled and pumped into the cell or tissue during the discharge.

In any case, the composition of the present invention can be directly utilized to deliver at least one biologically active agent selected from the group consisting of a polynucleotide construct, a nucleic acid, a peptide, a polypeptide, a plant hormone, an enzyme, a herbicidal agent, an anti-viral agent, anti-bacterial agent and an anti-fungal agent into a plant cell or a plant tissue by applying the stinging cells or capsules isolated therefrom, which include the biologically active agent, or by co-applying the biologically active agent and the stinging cell/capsule onto a plant tissue and triggering discharge either automatically (via contact with the tissue) or manually via an activation mechanism which is described in detail herein below.

Delivering a biologically active agent into a plant cell or tissue according to the methods of the present invention can be utilized for various purposes. For example, the delivery of a polynucleotide construct for the production of transgenic plants; delivery of labeled proteins to assist in elucidating their final destination within the plant cell; delivering molecular chaperones such as small Heat Shock Proteins to study their effect on the plant resistance to different abiotic stress conditions such as salt, osmotic, heat, cold, and UV; delivering different large or small molecules (organic and inorganic) from chemical libraries and screen for their effect on plant phenotype; delivering different enzymes that potentially modify metabolic pathways in plants. As the methods provide means for localized delivery, delivery of a couple of proteins into the same cell can show the interaction between the proteins. Delivery of a plurality of biologically active agents is not necessarily restricted to the same type of agent, e.g. a protein and a virus can be delivered to examine the effect of the protein on the virus replication, transmission and symptoms.

The compositions used in accordance with the methods of the present invention may be in a form selected from the group consisting of an aqueous solution, a gel, and a semi-solid formulation. To stabilize the active ingredients of the compositions of the present invention, i.e. the selected biologically active agent and/or the stinging cell(s)/capsule(s), and to possibly enhance triggering efficiency, the composition can further comprise biologically compatible carriers and/or stabilizers and activators. Although, for some applications, contact mediated discharge suffices, such activation can be inefficient since it enables discharge of only portion of the stinging cells, which come into physical contact with the tissue following application. To enable a more efficient and consistent discharge and thus delivery of the biologically active agent, the composition of the present invention can include a biologically compatible carrier/stabilizer which inhibits discharge of the stinging cell(s)/capsule(s) upon tissue contact. In such cases, the composition further includes a chemical activator, which can be applied prior to, or following, application of the delivery composition and which triggers discharge of the stinging cells.

Chemical triggering can be mediated by substances such as free and conjugated N-acetylated sugars or low molecular weight amino compounds which are known to be detected by at least two classes of stinging cell chemoreceptors. For example, Sodium thiocyanate (NaSCN) has been shown to be capable of triggering discharge of cnidocysts (U.S. Pat. No. 6,613,344). In addition, Lubbock and Amos (1981, supra) have shown that isolated cnida (cnidocysts) can discharge normally when placed in buffered EGTA or 10 mM citrate solution; Weber (1989. Eur J Biochem, 184(2):465-76) demonstrated the effect of dithioerthritol or proteases on discharging isolated cnida, and Hidaka (1993, supra) discussed various agents, which can trigger cnida discharge. Triggering may also be mediated by water.

Alternatively, tubule discharge can be triggered electrically. Electrical triggering can be achieved via an electrical pulse of 30 microseconds of approximately 20-30 Volts as is further described in the literature (Holstein and Tardent 1984, supra; Tardent and Holstein 1982. Cell Tissue Res, 224(2), 269-90).

Chemical or electrical activation of discharge is advantageous over contact triggering since it allows for simultaneous discharge of most if not all of the stinging cells of the composition.

As mentioned hereinabove, the methods of the present invention can be utilized to deliver a variety of biologically active agents, including nucleic acids. The effective delivery obtainable via stinging cells/capsules can be utilized for efficient polynucleotide construct transformation into the plant cell/tissue.

In the last two decades, transformation technology has played an increasingly important role in the genetic manipulation of crop plants for their improvement and in the study of the molecular mechanisms underlying plant gene expression and regulation. Methods for polynucleotide transfer into a plant cell are known in the art, and include, inter alia, *Agrobacterium*-mediated introduction, protoplast fusion, viral-mediated transformation, high velocity projectile introduction, electroporation, injection into reproductive organs, and injection into immature embryos. However, as described herein above, each of these defined methods has its limitations and disadvantages, and many plant species, including crop species, are still not amenable to genetic modifications due to the lack of a useable transformation procedure. Successful transformation of plant cells using the delivery compositions as described herein provide a new means for the introduction of foreign genes into plants, including transformation of plant species in which hitherto transformation could not be performed or performed at a very low efficiency.

Thus, according to another aspect, the present invention provides a method for transforming a plant cell or a plant tissue, the method comprising the steps of: (a) applying a composition comprising at least one polynucleotide construct to an outer surface of the plant cell or plant tissue; (b) applying at least one stinging capsule to the outer surface of said plant cell or said plant tissue; and (c) triggering a discharge of the at least one stinging capsule to thereby deliver the at least one polynucleotide construct into said plant tissue or plant cell to form a transformed plant cell or tissue.

According to one embodiment, the at least one polynucleotide construct and the at least one stinging capsule are applied as a single combined composition.

The exogenous polynucleotide can be either homologous or heterologous to the plant genome to which it is transformed. The introduced polynucleotide can modify the production and/or function of a polypeptide of interest, for example increasing the amount of a rate-limiting enzyme by introducing additional copies of the gene. A reduction in the level of a polypeptide of interest can be achieved by transforming the target plant with at least one antisense copy of a gene encoding the polypeptide, or a functional portion thereof, or alternatively by transforming small interfering RNAs (siRNAs) or a polynucleotide encoding same. Non-coding portions of polynucleotides, such as a regulatory polynucleotides and polynucleotides encoding regulatory factors such as transcription factors, and/or functional portions of a transcription factors, and/or antisense copy of such a regulatory factors, can also be introduced to the target plants to modulate the expression of certain polypeptides. An exogenous polynucleotide can also be introduced for the production of a foreign protein.

According to one embodiment, the polynucleotide construct further comprises at least one regulatory element to confer functional expression of the exogenous polynucleotide in the transformed plant. Expression of a polynucleotide refers to the process wherein a DNA region which is operably linked to appropriate regulatory element is transcribed into an RNA which is biologically active i.e., which is either capable of interaction with another polynucleotide or which is capable of being translated into a polypeptide or protein. As used herein, the term "polypeptide" encompasses amino acid chains of any length, including full-length proteins, wherein amino acid residues are linked by covalent peptide bonds.

According to one embodiment, the polynucleotide construct according to the present invention is built in such a way to further include at least one marker gene conferring the ability to select transformed cells and tissues regenerated therefrom, for example callus, embryos and mature plants.

According to another embodiment, the different elements of the construct may be included in separate DNA fragments rather than on a single DNA fragment and are then used together preferably as a single mixture for the transformation.

The delivery composition according to the present invention can be used to transform a plant cell with any polynucleotide of interest. As used herein "polynucleotide" means a polymeric collection of nucleotides and includes DNA and corresponding RNA molecules, both sense and anti-sense strands, and comprehends cDNA, genomic DNA and recombinant DNA, as well as wholly or partially synthesized polynucleotides. A polynucleotide may be an entire gene, or any portion thereof. Operable anti-sense polynucleotides may comprise a fragment of the corresponding polynucleotide, and the definition of "polynucleotide" therefore includes all such operable anti-sense fragments. Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthesizing method. The term polynucleotides refer to isolated and purified polynucleotides, as those terms are commonly used in the art.

When the polynucleotide construct comprises a coding portion of a polynucleotide, the polynucleotide construct further comprises a gene promoter sequence and a gene termination sequence operably linked to the polynucleotide to be transcribed. The gene promoter sequence is generally positioned at the 5' end of the polynucleotide to be transcribed, and is employed to initiate transcription of the polynucleotide. Promoter sequences are generally found in the 5' non-coding region of a gene but they may exist in introns or in the coding region. When the construct includes an open reading frame in a sense orientation, the gene promoter sequence also initiates translation of the open reading frame. For polynucleotide constructs comprising either an open reading frame in an antisense orientation or a non-coding region, the gene promoter sequence may comprise a transcription initiation site having an RNA polymerase binding site. The polynucleotide construct of the present invention can further comprise a reporter gene or a selection marker that is effective in the target plant cells to permit the detection of transgenic cells, tissues or plants containing the polynucleotide construct. Such selection markers and reporter genes, which are well known in the art, typically confer resistance to one or more toxins and encode for a detectable enzymatic activity, respectively. The nptII gene, whose expression results in resistance to kanamycin, or the hph gene whose expression results in resistance to hygromycin antibiotic, which are generally toxic to plant cells at a moderate concentration, can be used as a selection marker. Alternatively, the presence of the desired construct in transgenic cells may be determined by means of other techniques that are well known in the art, including PCR, Southern and Western blots.

Techniques for operatively linking the components of the polynucleotide constructs used to transform target plant materials are well known in the art and include the use of synthetic linkers containing one or more restriction endonuclease sites as described, for example, by Maniatis et al., (Molecular Cloning: A Laboratory Manual, Cold Spring Harbor Laboratories, Cold Spring Harbor, N.Y., 1989).

The cells or tissue transformed utilizing the methods of the present invention can be cultured as to regenerate a transgenic plant. Successful regeneration of such a transformed cell depends on the cell type and origin. Various methods can be used for the regeneration of a transformed plant cell into a plantlet and a mature plant, as known to a person skilled in the art.

According to a further aspect, the present invention provides a method of screening for activity of a biologically active agent within a plant tissue, the method comprising the steps of: (a) applying a composition comprising a plurality of stinging capsules comprising the biologically active agent onto a support in a predetermined pattern; (b) contacting the plant tissue with the plurality of stinging capsules; (c) triggering a discharge of said plurality of stinging capsules to thereby deliver said biologically active agent into said plant tissue and (d) detecting the activity of said biologically active agent within the plant cell.

Stinging cells or isolated capsules injecting a biologically active agent such as polynucleotide or a polypeptide can be utilized to transfer the biologically active agent into the plant tissue in a predetermined pattern. For such purpose, the predetermined pattern of stinging cells/capsules can be attached to a support such as foil, glass, plastic and the like. The stinging cells/capsules are preloaded with the biologically active agent that can be of one type or of a plurality of types. For example, the stinging capsules may contain the same or different nucleic acid sequences; each of the stinging capsules arranged in a pre-determined pattern can contain either nucleic acid or a polypeptide. Upon stinging cells/capsules discharge (via, for example contact with the plant tissue) the polynucleotide construct would penetrate into the plant tissue to form the predetermined pattern; the presence of the biologically active agent, such as polynucleotide or polypeptide within the plant tissue can be detected in situ by various methods, as is known to a person skilled in the art.

For example, such method can be utilized for screening for a polypeptide that can inactivate herbicide applied to the plant tissue and thus protect the plant from the deleterious effect of the herbicide, to obtain herbicide-resistant plant. Upon activation of the stinging capsules the candidate polypeptides are injected into the plant tissue (for example, plant leaf) in a specific pattern; spraying the leaf with the herbicide in question can then reveal un-damaged leaf areas, indicating the presence of an active anti-herbicidal polypeptide.

Additional objects, advantages, and novel features of the present invention will become apparent to one ordinarily skilled in the art upon examination of the following examples, which are not intended to be limiting.

EXAMPLES

Example 1

Isolation of Capsules

Fresh tentacles of *Rhopilema nomadica* are homogenized in seawater. 300 μl of the homogenate are added to 300 μl Percoll in a microfuge tube. The tube is placed over ice and shaken for 30 min and then centrifuged for 10 minutes at 1000 rpm. The pellet is washed 3 times with water and resuspended in 50 μl water. The capsules are kept at 4° C. until use.

Example 2

Inactivation of Capsule-stored Polypeptides

The temperature range that is tolerated by *Rhopilema nomadica* is between 16° C. to 30° C. Therefore, it is possible to perform denaturation and inactivation of an endogenous polypeptide at 45° C. Isolated capsules are incubated for 22 hours at 45° C. Following the heat inactivation process the capsules remain intact and their round shape is left unchanged. Moreover, the heated capsules are able to discharge normally upon treatment with NaSCN.

Example 3

Altering the Content of the Isolated Capsules

Loading the capsule with the biologically active agent, in this example a polynucleotide, is performed by incubating the isolated capsules with a polynucleotide fragment or plasmid in a water or suitable buffer solution for 3 minutes, in which the polynucleotide penetrates into the intact capsules. The solution containing the loaded capsules is used for the delivery of the polynucleotide into a plant tissue. Upon activation with NaSCN the capsules containing the polynucleotide will discharge normally and will release the polynucleotide fragment through the tubule into the target tissue. The polynucleotide fragment in this example contains the TDNA sequence of the pBIN121 (Clontec, Palo Alto Calif.), which includes the NPTII gene for antibiotic selection and the GUS reporter gene.

Example 4

Producing Transgenic *Nicotiana Tabaccum* Plants Expressing the GUS Gene

Plant Material and Growth Conditions

*Nicotiana tabaccum* (tobacco) plants are grown at 25-26° C. under a 16 h photoperiod, using cool-white fluorescent light (50-60 $\mu E\ m^{-2}\ S^{-1}$).

Isolation of Plant Nucleic Acids from Plant Tissue

DNA is extracted from stems and leaves as described by Doyle and Doyle (1987). RNA is extracted by "TRI-RE-AGENT™" (Molecular Research Center Inc., Cincinnati, Ohio), according to the manufacturer's instructions.

Production of Transgenic Tobacco Plants

*Nicotiana tabaccum* leaf-disks are used for the transformation. Leaf-disc preparation and treatment before and after transformation including regeneration media and selection are all done as previously described (DeBlock et al., 1984. Embo J, 3:1681-1689).

For DNA transformation disks of tobacco plant are used. Three types of leaf disks are prepared and used:

1. Non-wounded disks.
2. Leaf disks which have been scratched by a sharp blade.
3. Leaf disks which have been mixed with carborundum powder and shaken gently for 30 seconds in order to achieve a shallow surface wounding.

When leaf disks are ready, they are placed in a dish containing the solution comprising the loaded capsules. Discharge of the capsules is initiated in this example by the addition of NaSCN. Upon activation, the capsule discharge normally and releases the polynucleotide fragment through the tubule, a portion of the tubules penetrate through the plant tissue and deliver the polynucleotide fragment stored by the capsule into the plant cells.

In this example the nucleic acid construct is a construct containing the TDNA of the pBI121, which include the NPTII gene for antibiotic selection and the GUS gene as a visual marker (FIG. 1).

Successful gene transfer is demonstrated by histological GUS staining analysis of leaf disks within 4 days from transformation. Regeneration and selection of stable transgenic plants is done as previously described (DeBlock et al., 1984, supra) using kanamycin as a selectable marker. The presence of the gus gene in independent transgenic plants is analyzed by Southern blot (Sambrook et al., 1989, supra) and PCR using specific primers. The GUS gene expression is demonstrated by X-Gluc staining (Jefferson et al., 1987. EMBO J., 6(13):3901-3907).

Example 5

Producing Transgenic Eucalyptus Plants Expressing the GUS Gene

Plant Material and Growth Conditions

Eucalyptus (*Eucalyptus grandis×Eucalyptus urophylla* hybrid) plants are grown in tissue culture tubes at 25° C. under a 16 h photoperiod, using cool-white fluorescent light (50-60 $\mu m^{-2} S^{-1}$).

Production of Transgenic Plants

Leaf disks or stem fragments are used for transformation. Gene transfer is performed as in examples 3 and 4 herein above. Regeneration and selection of transgenic plants is done as previously shown by Tournier et al., 2003. Transgenic Res. 12(4):403-411). Transient and stable transformation and the successful production of transgenic plants are demonstrated as in example 4.

Thus, the teachings of the present invention can provide an efficient, rapid and targeted delivery of a biologically active agent selected from the group consisting of a polynucleotide, a peptide, a polypeptide and an enzyme, specifically for the transformation of a polynucleotide into a plant cell or a plant tissue.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

Example 6

Plant Transformation with Isolated Stinging Capsules

DNA Preparation

Figure 3:
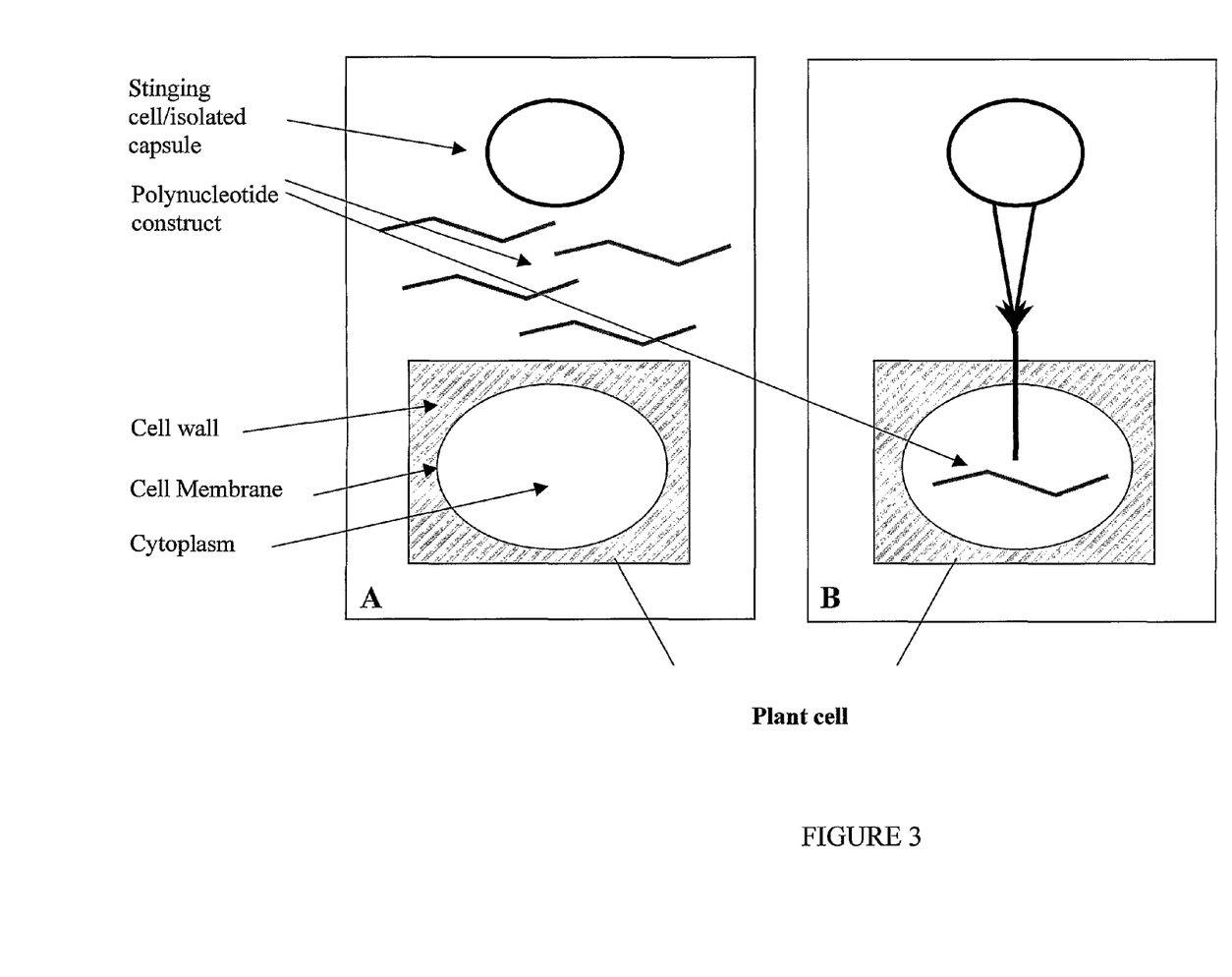
Figure 4:
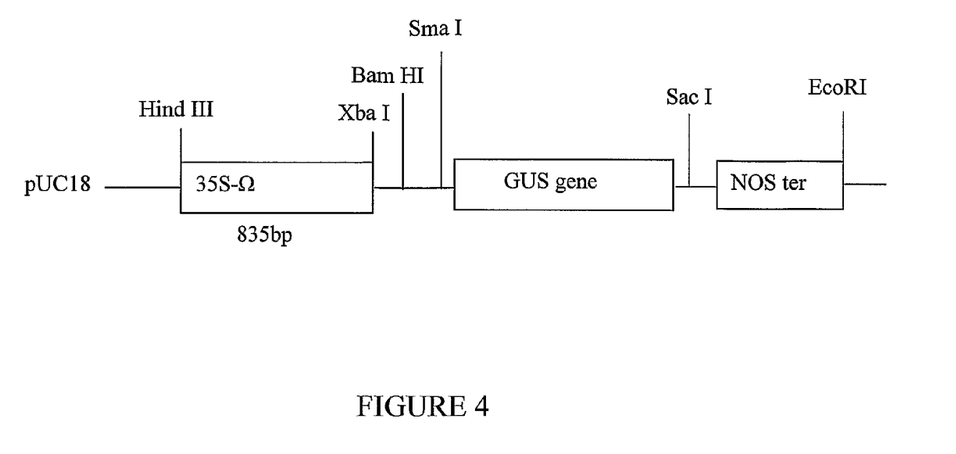
Figure 5:
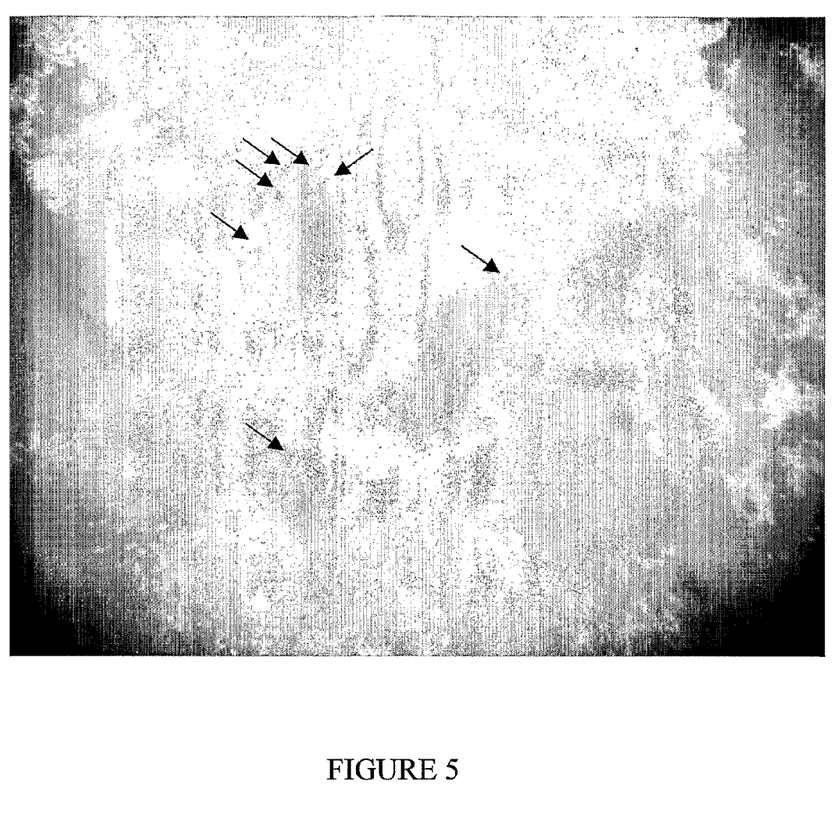
Figure 6:
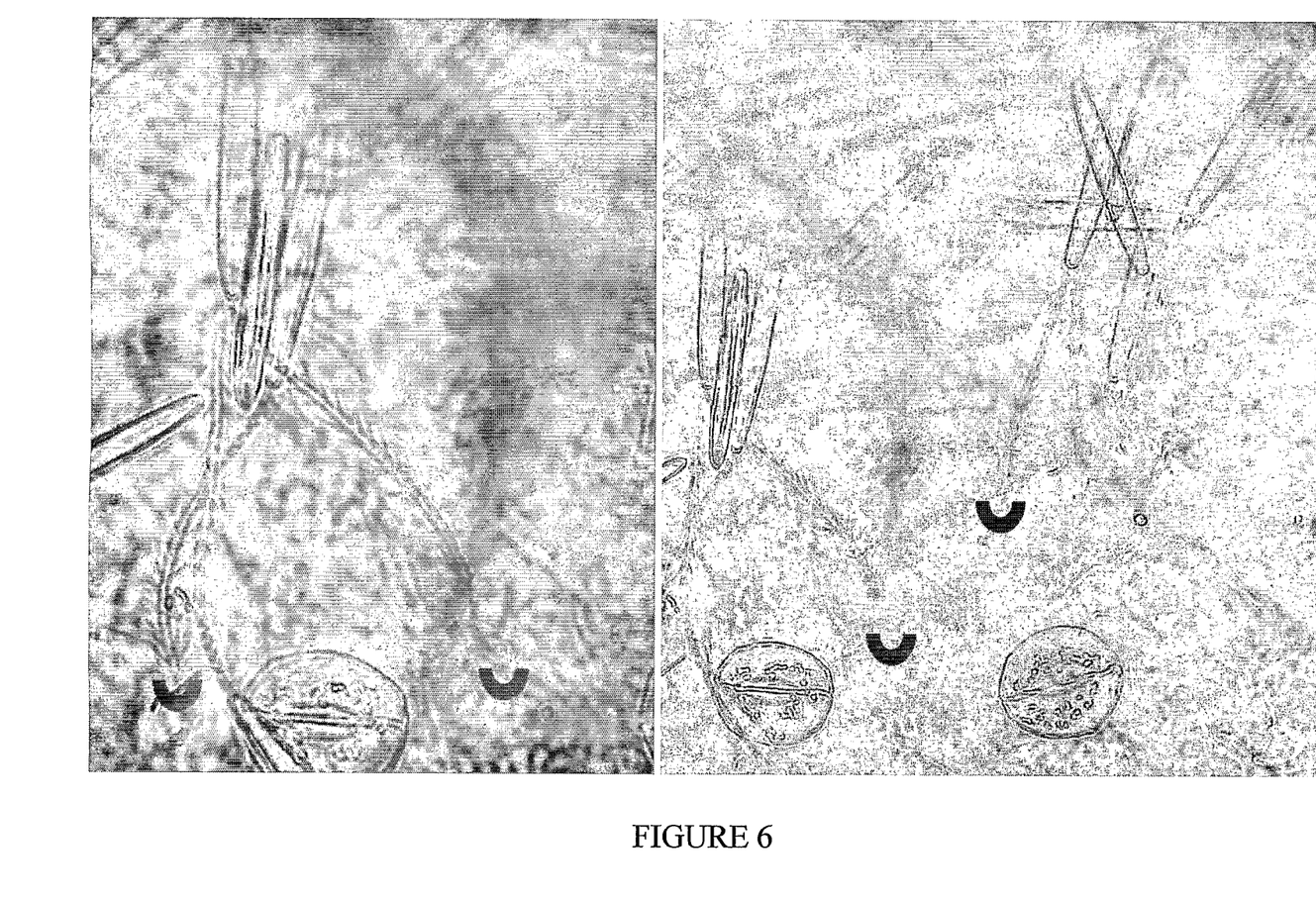

A DNA construct containing 35SΩ promoter and GUS gene was prepared as follow: The DNA fragment containing the GUS gene and the NOS terminator was isolated from the pBI121 construct using BamIII and EcoRI and was inserted into pUC18 plasmid, downstream of the 35SΩ promoter (FIG. 3). In order to isolate the 35SΩ-GUS-NOS terminator construct pUC-35SΩ-GUS-NOS terminator was digested with HindIII and EcoRI, the DNA was extracted by chloroform and ethanol precipitation and was resuspended by water. A mixture of the two DNA fragments was used for the plant transformation.

Plant Transformation

Transformation of tobacco leaves was applied as follow:

Tobacco leaves were cut into 2 cm2 pieces on filter paper in order to blot the liquid from inside and the humidity outside the leaf.

180 μg of digested DNA were dried and resuspended in the capsules suspension solution+0.03% Silwet. The solution was mixed well and added to the dry capsules.

The capsules were suspended in aliquots of 8 μl containing either 25,0000 or 125,000 capsules. The capsules (8 μl of two different dilution) were spread on the leaf surface and 3 μl of water were added immediately to activate the capsules. After the capsules activation the leaves were laid on TB medium (0.47% MS (Murashige and Skoog medium, Duchefa Biochemie, Haarlem, The Netherlands), 2% sucrose, 1% mannitol, 1% agar, 2 mg/l zeatin, 0.1 mg/l IAA, pH 5.8) and the plates were transferred to the tissue culture growth room at 26° C. After 24 hours the leaves were washed briefly in water; blotted dry and laid back onto a new plate.

Figure 1:
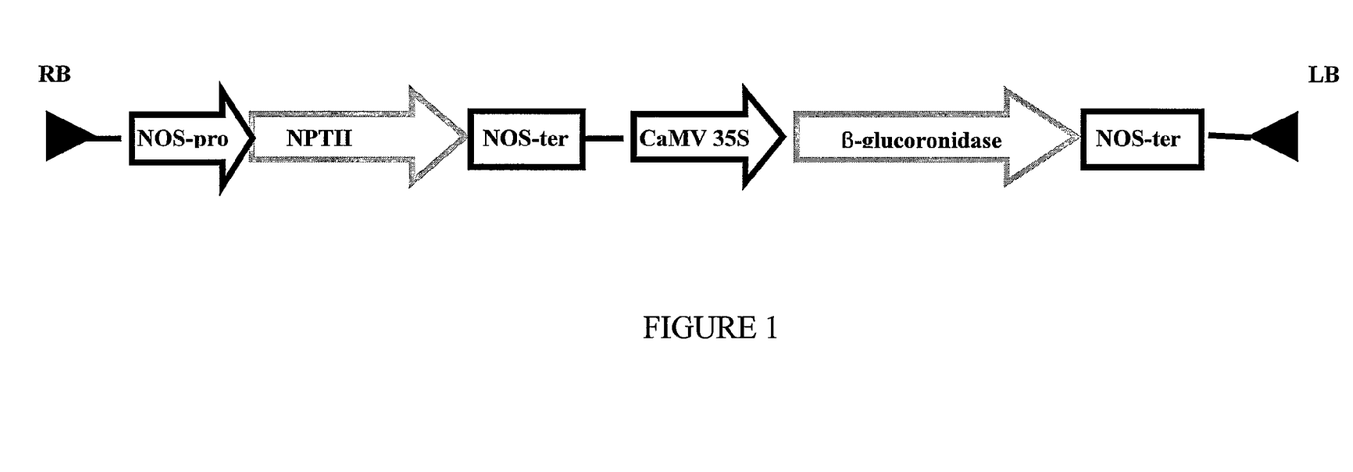
Figure 2:
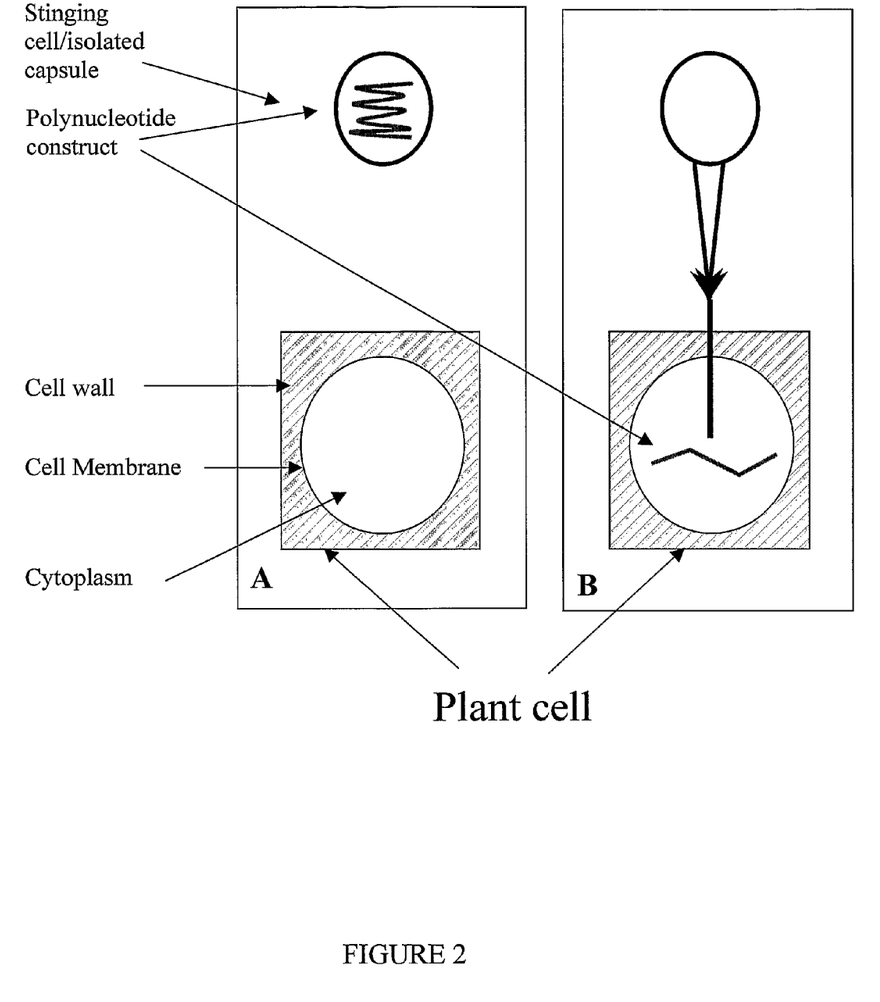

GUS stain was performed after 48 and 60 hours. Transformation occurred in both treatments but preferentially when 250,000 capsules were used. Transformed areas can be seen as small blue spots on the leaf surface (FIG. 2). When transformed leaves are observed under light microscope the capsules can be seen, some of the capsule's stings remain stuck inside the leaf cells (FIG. 3).

Histological GUS-staining Analysis of Transformed Explants

GUS staining was performed with X-Gluc (Duchefa Biochemie) as described previously (Jefferson et al., 1987). The explants were incubated overnight with X-Gluc solution at 37° C. and then kept in a 70% ethanol solution prior to photographing.

The invention claimed is:

1. A composition comprising at least one stinging capsule and at least one agent biologically active in a plant cell, wherein the stinging capsule is capable of delivering the at least one agent into a target plant cell or tissue and wherein said at least one agent is a polynucleotide construct capable of being expressed in the plant cell comprising at least one plant-specific regulatory element capable of functioning in said plant cell.

2. The composition of claim 1, wherein the at least one polynucleotide construct comprises at least one gene of interest.

3. The composition of claim 1, wherein the regulatory element is selected from the group consisting of a promoter, an enhancer, a terminator, a transposable element and a post-transcriptional element.

4. The composition of claim 2, wherein the at least one polynucleotide construct further comprises a selectable marker.

5. The composition of claim 4, wherein the marker and the gene of interest are present on separate DNA fragments.

6. The composition of claim 1, wherein the at least one polynucleotide construct is a DNA construct designed for generating siRNA.

7. The composition of claim 6, wherein the siRNA is selected from an siRNA which prevents flowering or effects changes in plant lignin composition.

8. The composition of claim 1, further comprising a biologically compatible carrier or stabilizer.

9. The composition of claim 1, wherein the polynucleotide construct is disposed in a liquid medium surrounding the at least one stinging capsule.

10. The composition of claim 1, wherein the polynucleotide construct is disposed in a liquid stored within the at least one stinging capsule.

11. The composition of claim 1, wherein the at least one stinging capsule is derived from an organism of a class selected from the group consisting of Anthozoa, Hydrozoa and Scyphozoa.

12. The composition of claim 1, wherein the at least one stinging capsule is derived from an organism of a phylum selected from the group consisting of Cnidaria, Dinoflagellata and Myxozoa.

13. The composition of claim 1, wherein the at least one stinging capsule forms a part of a stinging cell.

14. The composition of claim 13, wherein the stinging cell forms a part of a tentacle derived from an organism of the phylum Cnidaria.

15. The composition of claim 1, further comprising a medium or carrier selected from the group consisting of an aqueous solution, organic cosolvent solution, a gel and a semi-solid formulation.

16. The composition of claim 1, wherein an endogenous toxin naturally stored within the at least one stinging capsule is substantially non-toxic to plants or is non-functional.

17. A method for transforming a plant cell or a plant tissue, the method comprising the steps of: (a) applying at least one polynucleotide construct to an outer surface of the plant cell or plant tissue, wherein the polynucleotide construct is capable of being expressed in the plant cell and comprises at least one regulatory element capable of functioning in said plant cell; (b) applying at least one stinging capsule to the outer surface of said plant cell or said plant tissue; and (c) triggering a discharge of the at least one stinging capsule to thereby deliver the at least one polynucleotide construct into said plant cell or plant tissue to form a transformed plant cell or tissue.

18. The method of claim 17, wherein the at least one polynucleotide construct and the at least one stinging capsule are applied as a single combined composition.

19. The method of claim 17, wherein the at least one stinging capsule comprises the at least one polynucleotide construct.

20. The method of claim 17, wherein the at least one polynucleotide construct comprises a gene conferring a functional agricultural trait selected from the group consisting of a pest resistance, herbicide resistance, increased yield, fiber quality and improved digestibility.

21. The method of claim 20, wherein the at least one polynucleotide construct further comprises at least one regulatory element conferring expression of the polynucleotide in the plant cell, wherein the regulatory element is selected from the group consisting of a promoter, an enhancer, a terminator, a transposable element and a post-transcriptional element.

22. The method of claim 21, wherein the at least one polynucleotide construct further comprises a selectable marker.

23. The method of claim 22, wherein the selectable marker is a reporter gene selected from the group consisting of a gene coding for a fluorescent protein; a gene coding for a chemiluminescent protein; and a gene coding for a protein having a detectable enzymatic activity.

24. The method of claim 17, wherein the at least one polynucleotide construct further comprises a gene coding for an exogenous protein selected from an antibody chain, a pharmaceutical protein and an industrial protein.

25. The method of claim 17, wherein the polynucleotide construct is a DNA construct designed for generating siRNA.

26. The method of claim 17, wherein the at least one stinging capsule is derived from an organism of a class selected from the group consisting of Anthozoa, Hydrozoa and Scyphozoa.

27. The method of claim 17, wherein the at least one stinging capsule is derived from an organism of a phylum selected from the group consisting of Cnidaria, Dinoflagellata and Myxozoa.

28. The method of claim 17, wherein the at least one stinging capsule forms a part of a stinging cell.

29. The method of claim 28, wherein the stinging cell forms a part of a tentacle derived from an organism of the phylum Cnidaria.

30. The method of claim 17, wherein an endogenous toxin naturally stored within the at least one stinging capsule is substantially non-toxic to plants or is non-functional.

31. The method of claim 17, wherein triggering the discharge of the at least one stinging capsule is affected by at least one of a change in pH, a chemical substance, a mechanical force, an electrical force and a contact between the at least one stinging capsule and the outer surface of the plant cell or plant tissue.

32. A method of delivering at least one agent into a plant cell or plant tissue, wherein the agent is a polynucleotide construct capable of being expressed in the plant cell and comprises at least one regulatory element capable of functioning in said plant cell, the method comprising the steps of: (a) applying the at least one polynucleotide construct to an outer surface of said plant cell or plant tissue; (b) applying at least one stinging capsule to the outer surface of said plant cell or plant tissue; and (c) triggering a discharge of the at least one stinging capsule to thereby deliver said at least one polynucleotide construct into said plant cell or plant tissue.

33. The method of claim 32, wherein the at least one polynucleotide construct and the at least one stinging capsule are applied as a single combined composition.

34. The method of claim 32, wherein triggering the discharge of the at least one stinging capsule is affected by at least one of a change in pH, a chemical substance, a mechanical force, an electrical force and a contact between the at least one stinging capsule and the outer surface of the plant cell or plant tissue.

35. A method of producing transgenic plants, the method comprising the steps of: (a) applying at least one polynucleotide construct to an outer surface of a plant cell or plant tissue, wherein the polynucleotide construct is capable of being expressed in the plant cell and comprises at least one regulatory element capable of functioning in said plant cell; (b) applying at least one stinging capsule to the outer surface of the plant cell or the plant tissue; (c) triggering a discharge of the at least one stinging capsule to thereby deliver said at least one polynucleotide construct into said plant cell or plant tissue to form a stably transformed plant cell or tissue; and (d) regenerating a transgenic plant from the stably transformed cell or tissue.

36. The method of claim 35, wherein the at least one polynucleotide construct and the at least one stinging capsule are applied as a single combined composition.

37. A method of screening for expression of a nucleic acid within a plant tissue, the method comprising the steps of: (a) applying a composition comprising a plurality of stinging capsules comprising the nucleic acid onto a support in a predetermined pattern; (b) contacting the plant tissue with the plurality of stinging capsules; (c) triggering a discharge of said plurality of stinging capsules to thereby deliver said biologically active agent into said plant tissue; and (d) detecting the expression of said nucleic acid within said plant tissue.

38. The method of claim 37, wherein the nucleic acid is selected from the group consisting of a nucleic acid encoding a polypeptide, a small interfering mRNA, and an antisense RNA.

39. The method of claim 37, wherein each of the plurality of stinging capsules comprise the same nucleic acid.

40. The method of claim 37, wherein the plurality of stinging capsules comprise a plurality of nucleic acids.

41. The method of claim 37, wherein the support is selected from the group consisting of a foil, a glass and a plastic.

42. The method of claim 37, wherein the composition is formulated in a form selected from the group consisting of a gel and a semi-solid formulation.

43. The method of claim 37, wherein triggering the discharge of the at least one stinging capsule is affected by at least one of a change in pH, a chemical substance, a mechanical force, an electrical force and a contact between the at least one stinging capsule and the outer surface of the plant cell or plant tissue.

* * * * *